United States Patent
Allen et al.

(10) Patent No.: US 9,065,720 B2
(45) Date of Patent: Jun. 23, 2015

(54) MEDICAL DEVICE AND EXTERNAL DEVICE COORDINATION SYSTEMS AND METHODS

(71) Applicant: Roche Diagnostics Operations, Inc., Indianapolis, IN (US)

(72) Inventors: Janette E. Allen, Zionsville, IN (US); Carol J. Batman, Indianapolis, IN (US); David B. Markisohn, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 281 days.

(21) Appl. No.: 13/794,886

(22) Filed: Mar. 12, 2013

(65) Prior Publication Data

US 2014/0280690 A1   Sep. 18, 2014

(51) Int. Cl.
*H04L 12/24* (2006.01)
*A61B 5/00* (2006.01)
*A61B 5/145* (2006.01)
*G06Q 10/10* (2012.01)

(52) U.S. Cl.
CPC ............. *H04L 41/00* (2013.01); *A61B 5/0002* (2013.01); *A61B 5/14532* (2013.01); *G06Q 10/1091* (2013.01)

(58) Field of Classification Search
CPC ............... H04L 41/00; G06Q 10/1091; A61B 5/14532; A61B 5/0002
USPC .................................................. 709/217, 223
See application file for complete search history.

(56) References Cited

U.S. PATENT DOCUMENTS

| | | | |
|---|---|---|---|
| 6,418,346 B1 * | 7/2002 | Nelson et al. ................. 607/59 |
| 8,041,783 B2 * | 10/2011 | Rahn et al. ................... 709/220 |
| 2006/0036134 A1 | 2/2006 | Tarassenko et al. |
| 2007/0282175 A1 | 12/2007 | Urbaszek et al. |
| 2009/0256701 A1 * | 10/2009 | Chamberlain et al. ... 340/539.12 |
| 2011/0124996 A1 | 5/2011 | Reinke et al. |
| 2012/0266251 A1 * | 10/2012 | Birtwhistle et al. ............. 726/26 |
| 2013/0036415 A1 | 2/2013 | Birtwhistle |

FOREIGN PATENT DOCUMENTS

WO     2013097931     *  7/2013  ............ H04W 84/18

* cited by examiner

*Primary Examiner* — Kostas Katsikis
(74) *Attorney, Agent, or Firm* — Harness, Dickey (57) ABSTRACT

A method includes: confirming a wireless communication link between a medical device and a mobile computing device hosting an application; requesting identifying data for the medical device via the wireless communication link; and receiving identifying data for the medical device via the wireless communication link in response to the request. The method further includes: presenting an option to register the medical device on a display of the mobile computing device; receiving an affirmative indication to register the medical device; requesting input of patient identifiable data for a user of the medical device in response to receiving the affirmative indication to register; receiving patient identifiable data for the user of the medical device in response to the request for input; forming registration data from the patient identifiable data and the identifying data; and registering the medical device with a manufacturer of the medical device using the registration data.

18 Claims, 9 Drawing Sheets

MEDICAL DEVICE AND EXTERNAL DEVICE COORDINATION SYSTEMS AND METHODS

FIELD

The present disclosure relates to handheld medical devices and more particularly to data distribution and revocation systems and methods for coordinating operation of an external device with a handheld blood glucose (bG) measurement device.

BACKGROUND

Persons with diabetes have difficulty regulating blood glucose levels in their bodies. As a consequence, many of these persons carry specialized electronic meters, called blood glucose meters, which allow them to periodically measure their glucose levels and take appropriate action, such as administering insulin. These persons may also carry with them a portable communication device, such as a mobile phone, a personal digital assistant, a tablet or similar device. People often rely on their portable communication device as the primary means for planning, scheduling and communicating with others. As a result, most portable communication devices are equipped with sophisticated software which provides user-friendly means for viewings and inputting data.

User interfaces of handheld diabetes management devices, including blood glucose meters, may be limited to limit the complication associated with operating the diabetes management device. There is a need to enable a user to simply configure various parameters of a diabetes management device, simply register a diabetes management device, and/or allow the user to more comprehensibly analyze data obtained via a diabetes management device.

The background description provided herein is for the purpose of generally presenting the context of the disclosure. Work of the presently named inventors, to the extent it is described in this background section, as well as aspects of the description that cannot otherwise qualify as prior art at the time of filing, are neither expressly nor impliedly admitted as prior art against the present disclosure.

SUMMARY

In a first feature, an automated method for registering a medical device via an application residing on a mobile computing device is described. The method includes: confirming, by the mobile computing device, a wireless communication link between the medical device and the mobile computing device hosting the application; requesting, by the mobile computing device, identifying data for the medical device via the wireless communication link; and receiving, by the mobile computing device, identifying data for the medical device via the wireless communication link, the identifying data for the medical device received in response to the request for identifying data. The method further includes: presenting, by the mobile computing device, an option to register the medical device on a display of the mobile computing device; receiving, by the mobile computing device, an affirmative indication to register the medical device; and requesting, by the mobile computing device, input of patient identifiable data for a user of the medical device, the request for input being performed in response to receiving the affirmative indication to register. The method further includes: receiving, by the mobile computing device, patient identifiable data for the user of the medical device in response to the request for input; associating, by the mobile computing device, the patient identifiable data for the user with the identifying data for the medical device to form registration data for the medical device; and registering, by the mobile computing device, the medical device with a manufacturer of the medical device using the registration data.

In a second feature, a coordinated method to setup a medical device using an application residing on a mobile computing device is described. The method includes: establishing, by the mobile computing device, a wireless communication link between the medical device and the mobile computing device hosting the application; requesting, by the mobile computing device, identifying data for the medical device via the wireless communication link; receiving, by the mobile computing device, identifying data for the medical device via the wireless communication link, the identifying data for the medical device received in response to the request for identifying data; and presenting, by the mobile computing device on a display of the mobile computing device, a first option to synchronize a first date and time tracked by the medical device with a second date and time tracked by the mobile computing device. The method further includes: receiving, by the mobile computing device, a first indication to synchronize the first date and time with the second date and time; transmitting, by the mobile computing device, the second date and time tracked the mobile computing device via the wireless communication link to the medical device, the sending being performed in response to the first indication to synchronize the first date and time with the second date and time; presenting, by the mobile computing device, a second option to configure the medical device to automatically wirelessly transmit medical data on the display of the mobile computing device; receiving, by the mobile computing device, a second indication to configure the medical device to automatically wirelessly transmit medical data; and transmitting to the medical device, by the mobile computing device, a request to configure the medical device to automatically wirelessly transmit medical data, the transmission being performed in response to receiving the second indication. The method further includes: presenting on the display, by the mobile computing device, a third option to register the medical device with a manufacturer of the medical device; receiving, by the mobile computing device, a third indication to register the medical device; requesting, by the mobile computing device, input of patient identifiable data for a user of the medical device, the request for input being performed in response to receiving the third indication; receiving, by the mobile computing device, the patient identifiable data for the user of the medical device in response to the request for input; associating, by the mobile computing device, the patient identifiable data for the user with the identifying data for the medical device to form registration data for the medical device; and registering, by the mobile computing device, the medical device with the manufacturer of the medical device using the registration data.

In a third feature, a mobile computing device executing an application for coordinating operation of the mobile computing device with a handheld diabetes management device is described. The mobile computing device includes: a touchscreen display; a processor; and memory. The memory includes instructions that, when executed, cause the mobile computing device to: establish a wireless communication link between the handheld diabetes management device and the mobile computing device; receive identifying data for the handheld diabetes management device via the wireless communication link; request identifying data for the handheld diabetes management device via the wireless communication link; present a first option on the touchscreen display to synchronize a first date and time tracked by the handheld diabetes management device with a second date and time tracked by the mobile computing device; and transmit the second data and time via the wireless communication link to the handheld diabetes management device in response to a first indication to synchronize the first date and time with the second date and time. When executed, the instructions further cause the mobile computing device to: present a second option on the touchscreen display to configure the handheld diabetes management device to automatically wirelessly transmit medical data; transmit, to the handheld diabetes management device, a request to configure the handheld diabetes management device to automatically wirelessly transmit medical data in response to a second indication to configure the handheld diabetes management device to automatically wirelessly transmit medical data; present a third option on the touchscreen display to register the handheld diabetes management device with a manufacturer of the handheld diabetes management device; present a request on the touchscreen display to input of patient identifiable data for a user of the handheld diabetes management device in response to a third indication to register the handheld diabetes management device; and transmit the identifying data and the patient identifiable data to a registration server.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
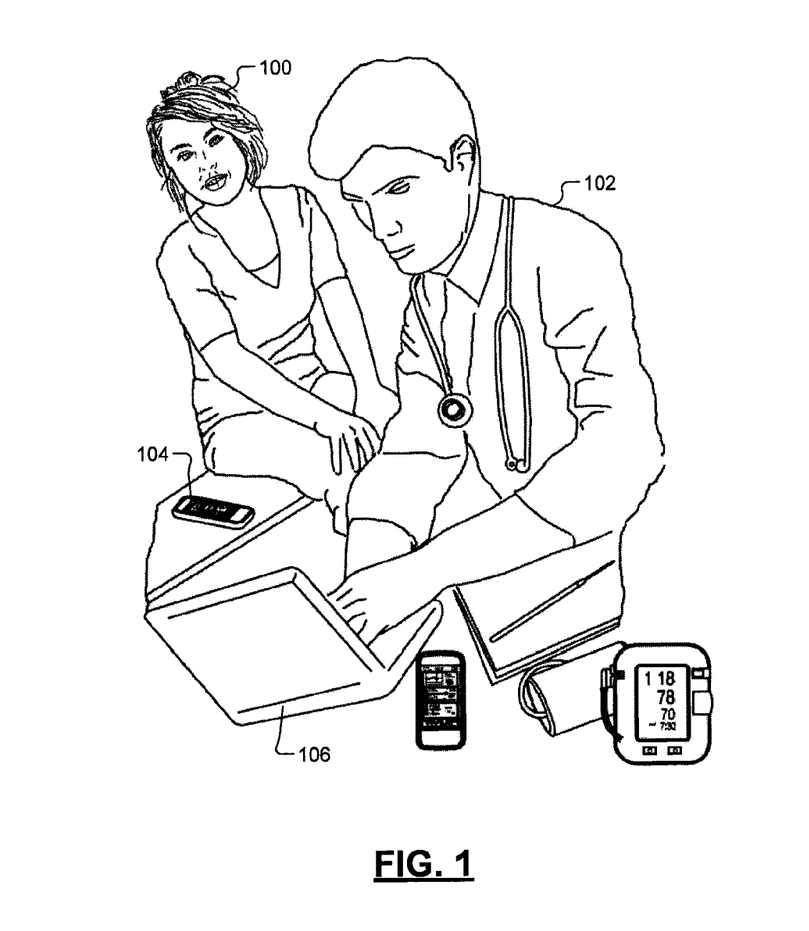
FIG. 1 shows a patient and a health care professional along with various devices that can be used to help the patient monitor and control health.

Referring now to FIG. 1, a patient 100 with diabetes and a health care professional 102 are shown in a clinical environment. The patient 100 with diabetes can be diagnosed with a metabolic syndrome, pre-diabetes, type 1 diabetes, type 2 diabetes, gestational diabetes, etc. Healthcare providers for diabetes are diverse and include nurses, nurse practitioners, physicians, endocrinologists, and others and are collectively referred to as health care professionals.

During a health care consultation, the patient 100 typically shares with the health care professional 102 a variety of data including blood glucose (bG) measurements, continuous glucose monitor data, amounts and type of insulin administered, amounts of food and beverages consumed, exercise schedules, health status, and other lifestyle information. The health care professional 102 can obtain additional data for the patient 100, such as measurements of HbA1C, cholesterol levels, plasma glucose, triglycerides, blood pressure, and weight. The data can be recorded manually or electronically on a handheld diabetes management device 104 (e.g., a handheld bG monitor device), diabetes analysis software executed on a personal computer (PC) 106, and/or a web-based diabetes analysis site. The health care professional 102 can analyze the patient data manually or electronically using the diabetes analysis software and/or the web-based diabetes analysis site. After analyzing the data and reviewing how efficacious previously prescribed therapy is and how well the patient 100 followed the previously prescribed therapy, the health care professional 102 can decide whether to modify a therapy prescribed for the patient 100.

Figure 2:
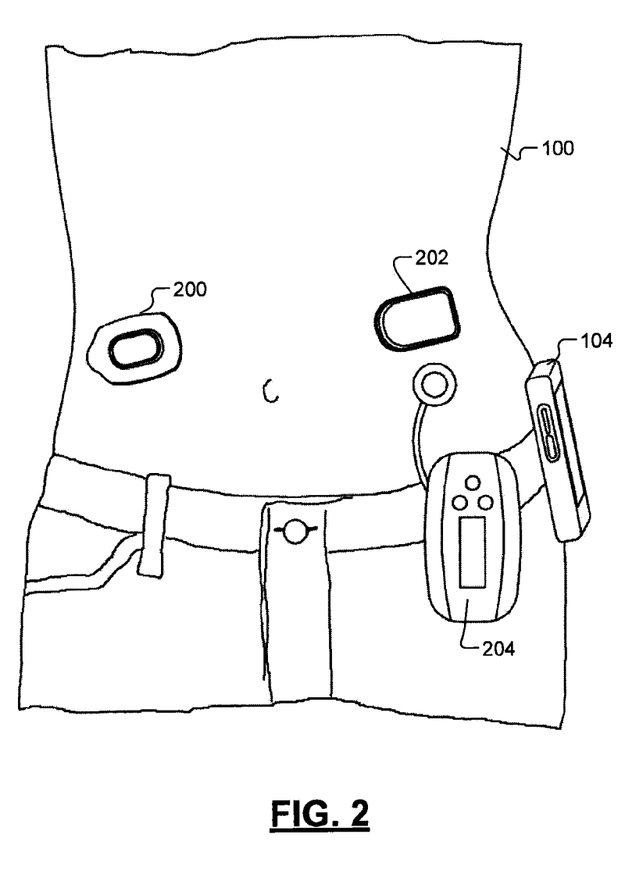
FIG. 2 shows a patient with a continuous glucose monitor (CGM), an ambulatory durable insulin infusion pump, an ambulatory non-durable insulin infusion pump, and a blood glucose (bG) management device.

Referring now to FIG. 2, the patient 100 can use a continuous glucose monitor (CGM) 200, an ambulatory durable insulin infusion pump 204 or an ambulatory non-durable insulin infusion pump 202 (collectively insulin pump 204), and the diabetes management device 104. The CGM 200 can use a subcutaneous sensor to sense and monitor the amount of glucose (e.g., glucose concentration) of the patient 100. The CGM 200 communicates glucose measurements to the diabetes management device 104.

The diabetes management device 104 performs various tasks including measuring and recording bG measurements, determining an amount of insulin to be administered to the patient 100 via the insulin pump 204, receiving user input via a user interface, archiving data, performing structured bG tests, etc. The diabetes management device 104 can transmit instructions to the insulin pump 204, and the insulin pump 204 selectively delivers insulin to the patient 100. Insulin can be delivered in the form of a meal bolus dose, a correction bolus dose, a basal dose, etc.

Figure 3:
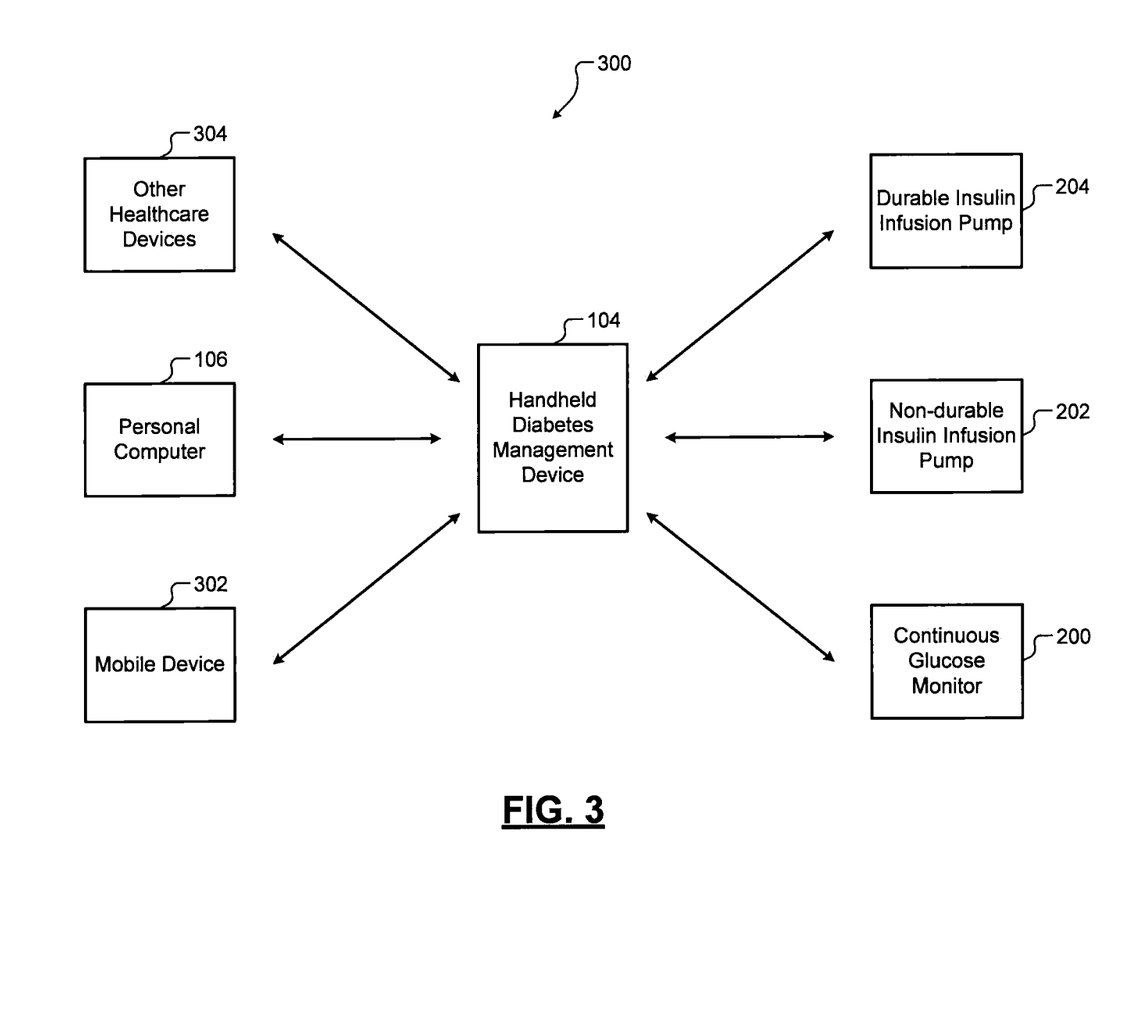
FIG. 3 shows a diabetes care system of systems that can be used to manage diabetes.

Referring now to FIG. 3, a diabetes management system 300 is shown which can be used by the patient 100 and/or the health care professional 102. The system 300 can include one or more of the following devices: the diabetes management device 104, the CGM 200, the insulin pump 204, a mobile device 302, the diabetes management software executed on the computer 106, and one or more other health care devices 304.

The diabetes management device 104 can be configured as a system "hub" and communicate with one or more of the other devices of the system 300. The insulin pump 204, the mobile device 302, or another suitable device can alternatively serve as the system hub. Communication between various devices in the system 300 can be performed using wireless interfaces (e.g., Bluetooth) and/or wired interfaces (e.g., USB). Communication protocols used by these devices can include protocols compliant with the IEEE 11073 standard as extended using guidelines provided by Continua Health Alliance Design Guidelines. Further, health care records systems such as Microsoft HealthVault™ and Google Health™ can be used by the patient 100 and the health care professional 102 to exchange information.

Figure 4:
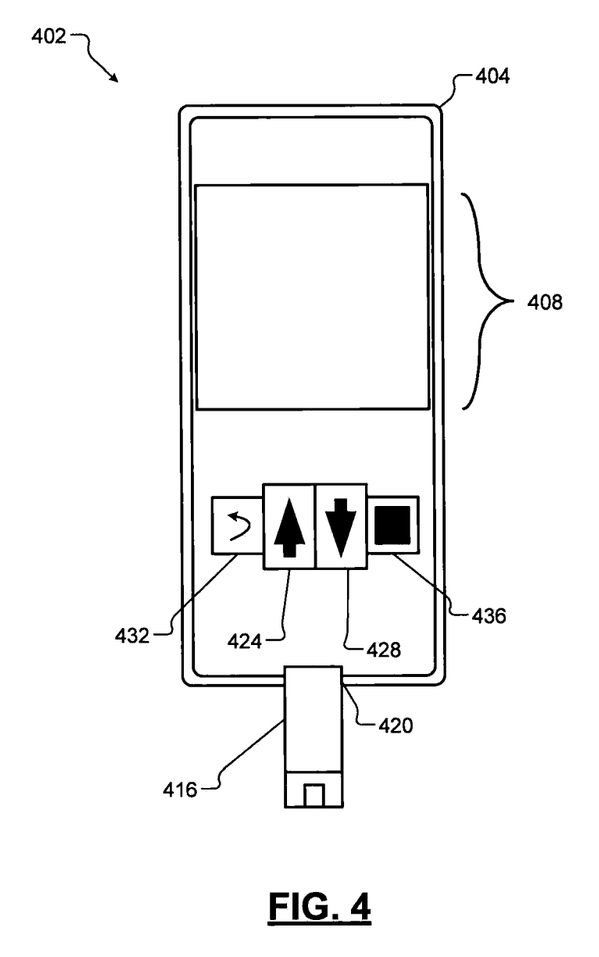
FIG. 4 is a high level diagram of an example implementation of a diabetes management device.

Referring now to FIG. 4, a high level illustration of an example embodiment of a (handheld) diabetes management device 402 is presented. The diabetes management device 402 includes, among other things, a housing 404, a display 408, a bG test strip port 420, and a bG test strip drum (not shown). The bG test strip drum may house a plurality of bG test strips, such as bG test strip 416. The diabetes management device 402 also includes user interface switches/buttons, such as up button 424, down button 428, back button 432, and enter button 436. The user interface switches/buttons can also include other buttons or switches, for example, ON/OFF switches and/or one or more other switches/buttons or other types of control devices that a patient can use to control functions/operations of the diabetes management device 104.

The bG test strip 416 can be inserted into the bG test strip port 420 by a user. The bG test strip 416 is shown already inserted into the bG test strip port 420 in the example of FIG. 4 and not yet inserted into the bG test strip port 420 in the example of FIG. 5. The display 408 of the diabetes management device 402 may be a non-touch screen display in various implementations. Various information may be selectively displayed on the display 408. For example, a bG measurement may be displayed on the display 408 when a bG measurement is made in response to insertion of a bG test strip.

The above description is a broad description of the diabetes management device 402. In practice, the diabetes management device 402 can include additional controls, input ports, output ports, etc., as can be desired to further enhance its utility or its use with other components and devices (e.g., computers, infusion pumps, cellular phones, etc.). The description of the diabetes management device 402 should not be taken as limiting as to the construction of the diabetes management device 402 or as to the features and capabilities of the diabetes management device 402.

Figure 5:
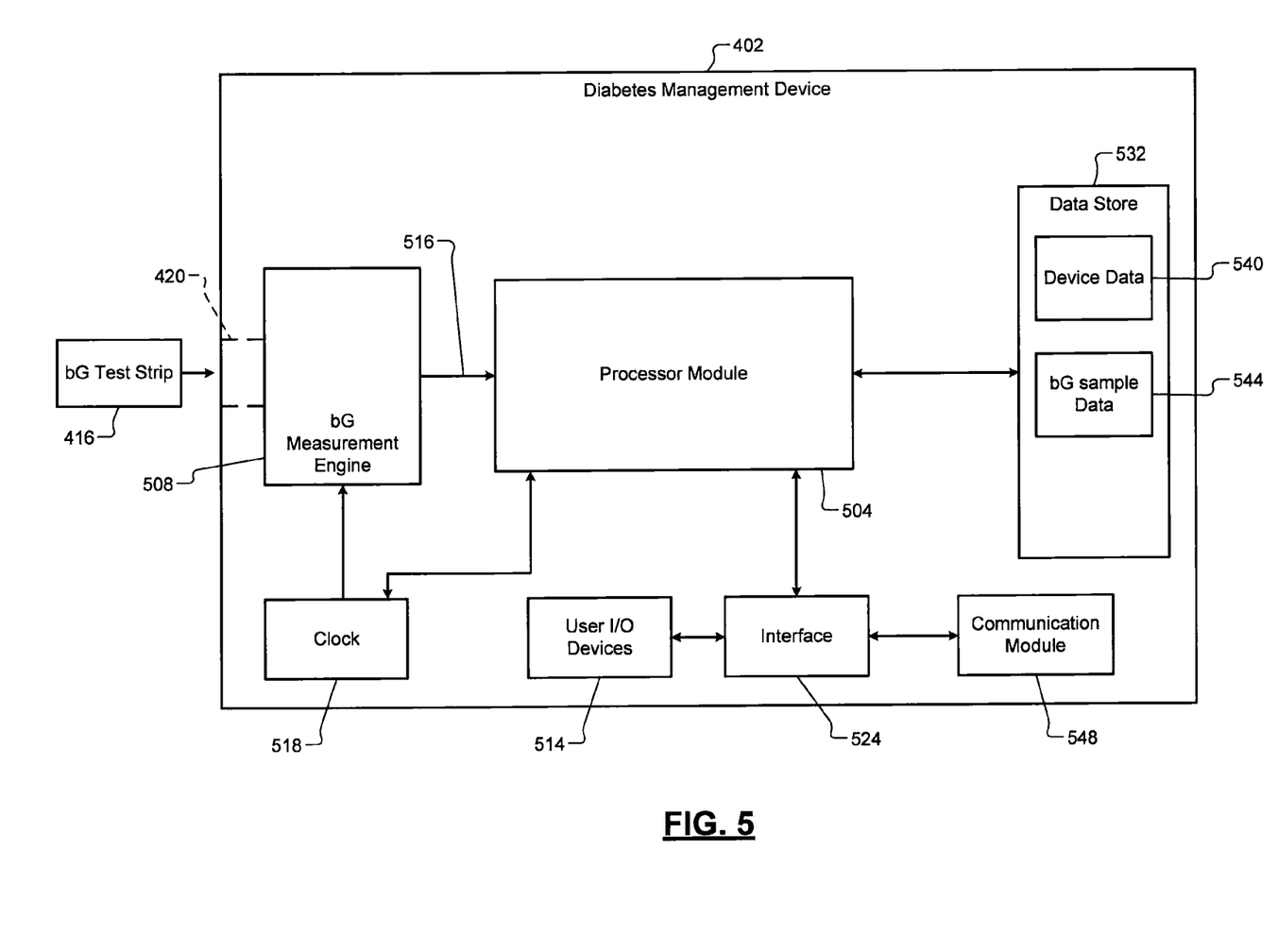
FIG. 5 includes a functional block diagram of an example implementation of a diabetes management device 402.

Referring now to FIG. 5, a functional block diagram of an example implementation of the diabetes management device 402 is presented. The diabetes management device 402 can include a processor module (e.g., a microprocessor based subsystem) 504 that can receive information from a bG measurement engine 508. The bG measurement engine 508 can be located adjacent the bG test strip port 420.

The bG measurement engine 508 reads (measures) a bG level of the bG test strip 416 inserted into the bG test strip port 420. The processor module 504 may power up other components of the diabetes management device 402, such as the display 408 and/or one or more other components, in response to insertion of a bG test strip into the bG test strip port 420 or actuation of an ON/OFF button or switch.

The bG measurement engine 508 generates bG sample data 516 based on its reading of the bG test strip 416. Among other things, the bG sample data 516 includes data indicative of the bG level of a bodily fluid sample on the bG test strip 416. The processor module 504 may also receive bG sample data from other sources, such as via the CGM 200, and/or another suitable source. The processor module 504 can receive user input via one or more user input/output (I/O) devices 514, such as the buttons 424-436.

The bG measurement engine 508 can also generate the bG sample data 516 to indicate the date and time when the bG test strip 416 was read. In other words, the bG measurement engine 508 can include a time stamp with the bG sample data 516. In various implementations, the processor module 504 can selectively time stamp the bG sample data 516 and can time stamp user input data and other data when it is received. A clock 518 can provide the date and time. Setting the date and time of the clock 518 is discussed further below, and the clock 518 can thereafter track the present date and time.

The bG measurement engine 508 may also stamp the bG sample data 516 with a sample identifier that is selected in a predetermined sequence. Based on the sample identifiers of sample data received from the diabetes management device 402 and the predetermined sequence, an external device can determine whether it has received all of the sample data stored by the diabetes management device 402. If less than all of the sample data has been received from the diabetes management device 402, the external device can identify which sample data it has not yet received and obtain (e.g., just) that sample data from the diabetes management device 402. An example of such a system and method can be found in commonly assigned U.S. patent application Ser. No. 13/195,884, filed on Aug. 2, 2011, which is incorporated herein in its entirety.

The diabetes management device 104 includes a datastore 532. For example only, the datastore 532 may include memory and/or one or more other suitable tangible, computer readable mediums. Various data may be stored in the datastore 532, such as device data 540. The device data 540 may include, for example, product type data, product version data, region data, a software certificate, a unique device identifier, a device/user certificate, and other suitable device specific data. The product type data may indicate, for example, diabetes management device, insulin pump, CGM, etc. The product version data may indicate, for example, a version (or generation) of the diabetes management device 402, a model name/number, etc. The software certificate may include, for example, a version or identifier of software executed by the diabetes management device 402. The unique device identifier may include data that is unique to the diabetes management device 402, such as a serial number and/or another suitable unique identifier.

bG sample data 544 and other types of data may also be stored in the datastore 532. The bG sample data 544 may include bG sample data generated by the bG measurement engine 508, such as bG sample data 516. The bG sample data 544 may also include other types of data related to bG samples.

One or more I/O interfaces, such as I/O interface 524, facilitate communication between the user I/O devices 514 and the processor module 504. The I/O interfaces may also facilitate communication between the processor module 504 and one or more communication modules, such as communication module 548. The communication module 548 may include a wireless transceiver and communicate (transmit and receive) wirelessly via one or more antennas.

Figure 6A:
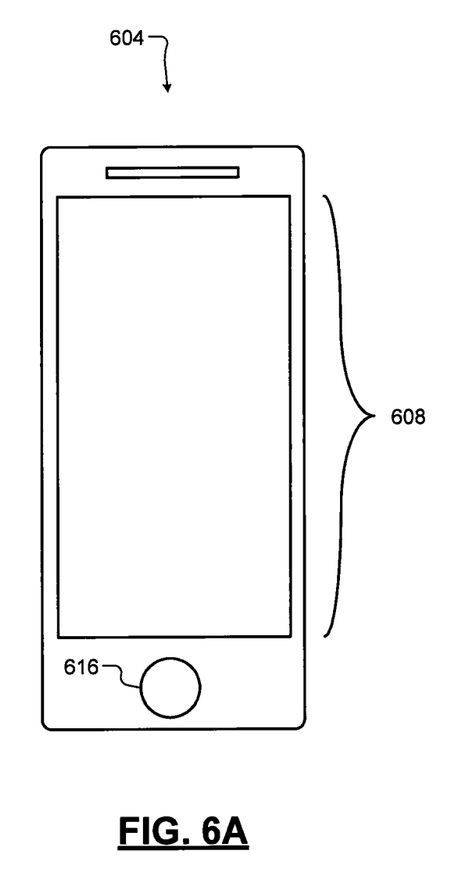
FIG. 6A is a high level illustration of an example implementation of a mobile device.
Figure 6B:
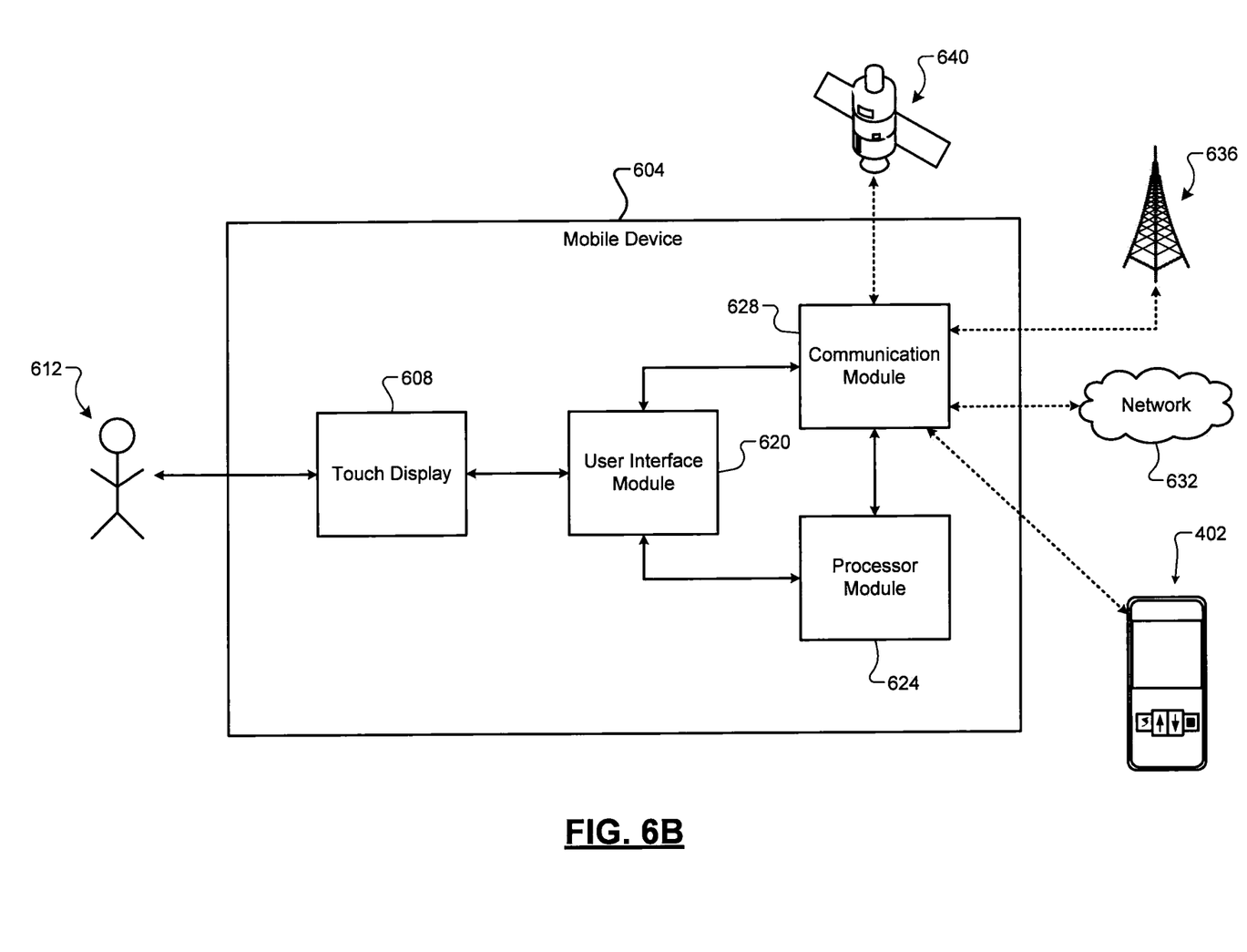
FIG. 6B is a functional block diagram of an example communication system including the mobile device of FIG. 6A and the diabetes management device of FIGS. 4-5.

FIG. 6A is a high level illustration of an example embodiment of a mobile device 604. FIG. 6B is a functional block diagram of a communication system including the mobile device 604 and the diabetes management device 402. Referring now to FIGS. 6A and 6B, the mobile device 604 may be any type of mobile/portable computing device, such as a mobile phone (as shown), a tablet computer, a laptop computer, a portable media player, etc.

The mobile device 604 includes a display 608. The display 608 may be a touch display as shown and will be referred to as a touch display. The touch display 608 may include any touch-sensitive display device, such as a capacitive sensing display. The mobile device 604 may additionally or alternatively include a physical character layout, such as a partial QWERTY-based keyboard (not shown).

The touch display 608 may display information to a user 612 and receive input from the user 612. For example only, the physical character layout may displayed on a portion of the touch display 608 as needed as a "soft keyboard", and the user 612 may input information to the mobile device 604 via the touch display 608 using one or more fingers. The user 612 may additionally or alternatively input information to the mobile device 604 via the touch display 608 using a stylus, a mouse, a trackball, or the like. The user 612 may additionally or alternatively interface the mobile device 604 via one or more user input devices, such as user input device 616.

The mobile device 604 may include or be connected to one or more audio output devices (not shown), such as one or more speakers. The mobile device 604 may include one or more audio input devices (also not shown), such as one or more microphones. The mobile device 604 may audibly communicate information to the user 612 via the audio output device(s). For example, the mobile device 604 may audibly communicate the level of bG measurements, reminders, etc. to the user 612. The mobile device 604 may receive input from the user 612 via the audio input device(s).

The mobile device 604 may further include a user interface module 620, a processor module 624, and a communication module 628. It should be appreciated that the mobile device 604 may include additional computing components such as a datastore and a power supply and that the functionality of the user interface module 620 and the communication module 628 may be executed in whole or in part by the processor module 624. Thus, the terms user interface module 620, processor module 624, and communication module 628, as used herein may include one or more processors executing instructions to perform the described functions.

The user interface module 620 can control communication with the user 612 via the touch display 608. The user interface module 620 may provide the user 612 with various different display configurations via the touch display 608. For example, the user interface module 620 may selectively provide the user 612 with a partial or whole standard QWERTY keyboard via the touch display 608. Different portions or functions of a standard QWERTY keyboard may also be selectively displayed via the touch display 608.

The processor module 624 controls most operations of the mobile device 604 and may communicate with both the user interface module 620 and the communication module 628. For example, the processor module 624 may perform tasks such as, but not limited to, loading/controlling the operating system of the mobile device 604, loading/executing programs and functions, loading/configuring communication parameters for the communication module 628, and controlling data storage/retrieval operations. While the processor module 624 is shown, the processor module 624 may include a plurality of individual processors operating in a parallel or distributed configuration can be utilized instead of a single processor. Thus, the term processor used herein may refer to one or more processors operating to perform the functions described.

The communication module 628 controls communication between the mobile device 604 and other devices and systems. The communication module 628 may be configured to communicate using both wired communication protocols (e.g., Universal Serial Bus) and wireless communication protocols (e.g., I.E.E.E. 802.XX, cellular, etc.). The communication module 628 communicates wirelessly via one or more antennas. The communication module 628 may communicate, for example, with a computing network 632, such as the Internet (hereinafter "the network 632"), a mobile telephone (cellular) network 636, a satellite network 640, and/or other types of communication devices or systems.

The communication module 628 can also wirelessly communicate with the diabetes management device 402. The communication module 628 and the diabetes management device 402 may wirelessly communicate using any wireless communication protocol, such as Bluetooth, Bluetooth Low Energy, radio frequency (RF), near field communications (NFC), etc.

The mobile device 604 may execute a diabetes management application in response to user input to the mobile device 604. The diabetes management application is embodied as code residing in a computer-readable medium that is executed by one or more processors of the mobile device 604. The diabetes management application is designed for use with diabetes management devices, such as the diabetes management device 402. By way of the diabetes management application, the user 612 can synchronize the date and time of the diabetes management device 402 with the date and time of the mobile device 604, enable automatic synchronization of the date and time with the diabetes management device 402 with the date and time of the mobile device 604, enable automatic transfers of bG sample data stored by the diabetes management device 402 to the mobile device 604, register the diabetes management device 402, review and analyze received bG sample data, and obtain other relevant information regarding diabetes management.

Figure 7:
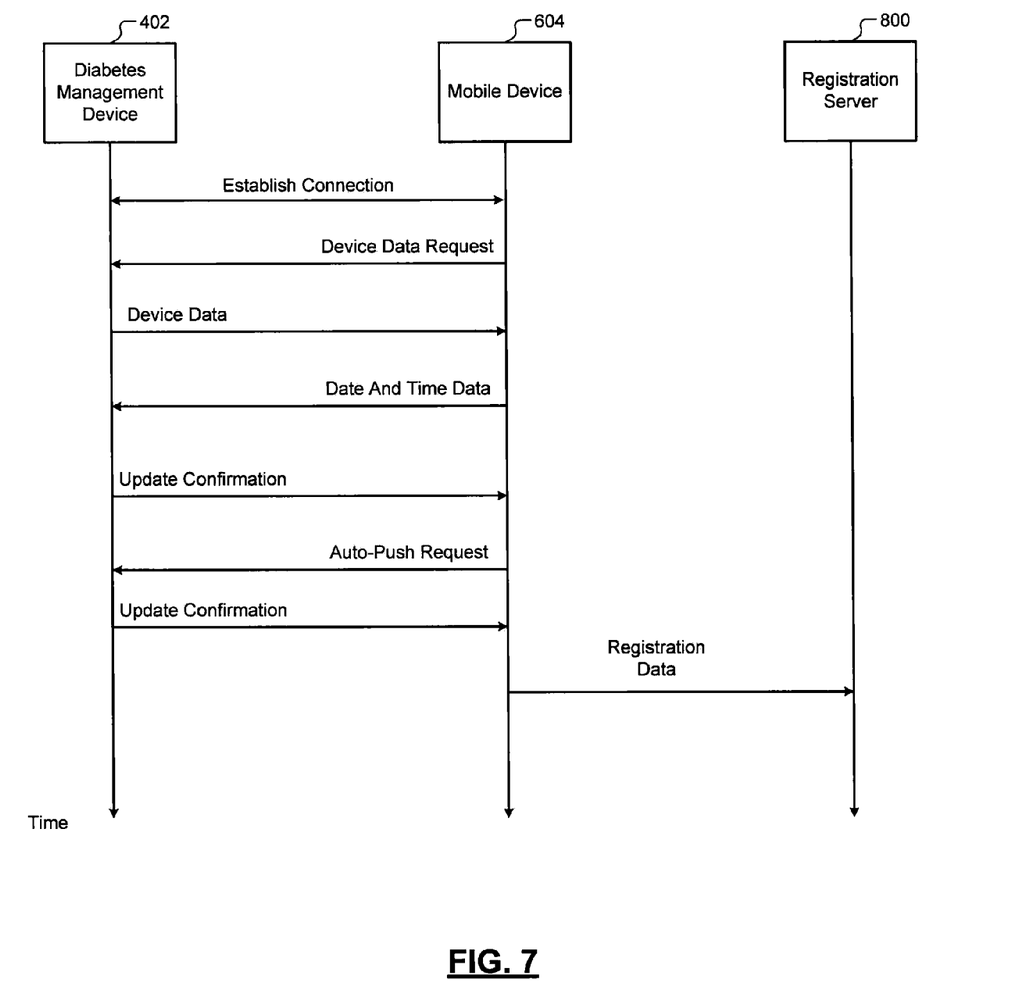
FIG. 7 is a sequence diagram illustrating example communications that may occur between the mobile device and the diabetes management device to coordinate operation of a diabetes management application executed by the mobile device with operation of the diabetes management device.
Figure 8A:
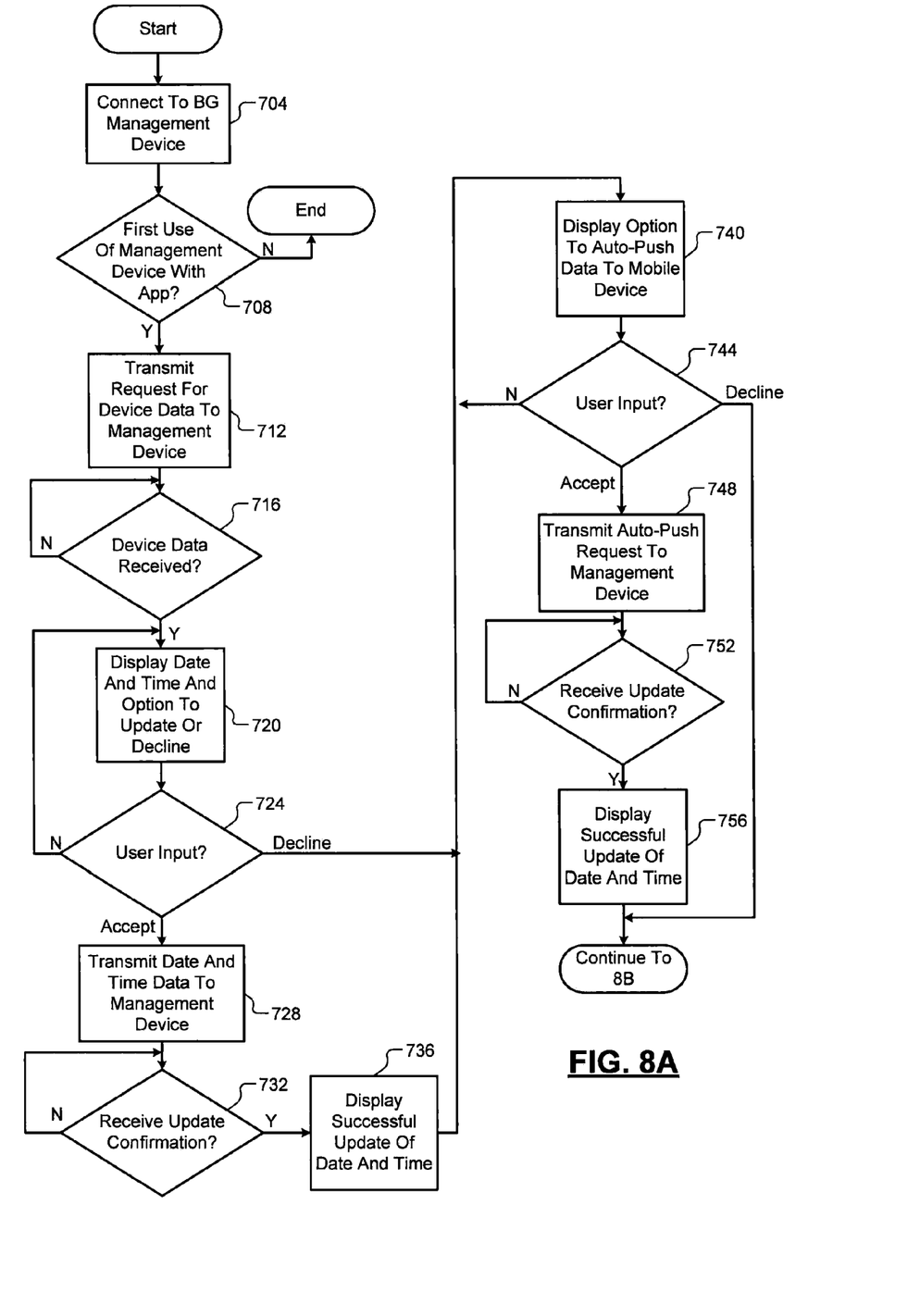
FIGS. 8A and 8B include a flowchart depicting an example method that may be performed by the mobile device.
Figure 8B:
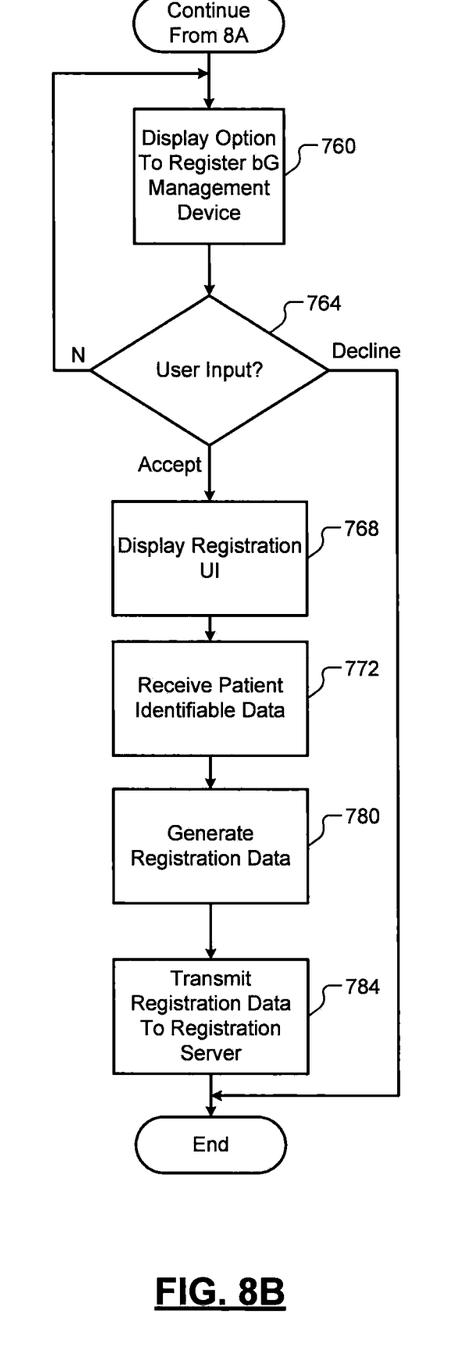

FIG. 7 is a sequence diagram illustrating communications that may occur between the mobile device 604 and the diabetes management device 402 to coordinate operation of the diabetes management application with operation of the diabetes management device 402. FIGS. 8A and 8B include a flowchart depicting an example method that may be performed by the mobile device 604 when executing the diabetes management application. The sequence diagram of FIG. 7 will be explained in conjunction with FIGS. 8A and 8B.

Referring now to FIGS. 8A and 8B, control may begin, for example, when the diabetes management device 402 is powered on and the mobile device 604 is executing the diabetes management application. The processor module 504 may power up the diabetes management device 402, for example, when a user actuates an ON/OFF button/switch of the diabetes management device 402 or when a bG strip is inserted into the bG test strip port 420.

At 704, the mobile device 604 may establish a wireless data connection (or link) with the diabetes management device 402. The mobile device 604 may determine whether this is the first instance of use of the diabetes management device 402 with the diabetes management application at 708. If 708 is true, control continues with 712. If 708 is false, configuration of the diabetes management device 402 may end.

The mobile device 604 wirelessly transmits a request for device data to the diabetes management device 402 at 712. The device data of the diabetes management device 402 may include, for example, data indicative of a model of the diabetes management device 402, a serial number of the diabetes management device 402, and other suitable data indicative of characteristics of the diabetes management device 402.

At 716, the mobile device 604 may determine whether the device data has been received from the diabetes management device 402. If 716 is true, control continues with 720. If 716 is false, control may remain at 716. If the device data has not been received for a predetermined period after the request for the device data was transmitted, the mobile device 604 may re-transmit the request for the device data, timeout, or take one or more other suitable actions.

At 720, the mobile device 604 displays its current date and time on the touch display 608 along with a question to the user 612, the question being directed to whether to update the date and time tracked by the clock 518 to the date and time tracked by the mobile device 604. The user 612 can select to update the date and time tracked by the clock 518 or decline to update the date and time tracked by the clock 518 via predetermined areas on the touch display 608 or providing other suitable user inputs.

The diabetes management device 402 may also display the question of whether to update the date and time tracked by the clock 518 to the date and time tracked by the mobile device 604 on the display 408 of the diabetes management device 402. The user 612 may select to update the date and time tracked by the clock 518 or decline to update the date and time tracked by the clock 518 via the diabetes management device 402. If the user 614 inputs his or her selection via the diabetes management device 402, the diabetes management device 402 wirelessly transmits an indicator of the selection to the mobile device 604.

At 724, the mobile device 604 determines whether the user 612 has input his or her selection as to whether to update the clock 518 of the diabetes management device 402. If not, control may return to 720 to continue displaying the question. If the user has not input his or her selection for a predetermined period, the mobile device 604 may timeout and end or take one or more other suitable actions. If the user 612 has indicated to update the clock 518 of the diabetes management device 402 to the date and time tracked by the mobile device 604, control continues with 728. If the user 612 has declined to update the clock 518 of the diabetes management device 402 to the date and time tracked by the mobile device 604, control may transfer to 740 (discussed further below) or configuration of the diabetes management device 402 may end.

At 728, the mobile device 604 wirelessly transmits a request to update the date and time tracked by the clock 518 and data indicative of the date and time tracked by the mobile device 604 to the diabetes management device 402. The diabetes management device 402 updates the current date and time tracked by the clock 518 to the date and time tracked by the mobile device 604 in response to receipt of the request and the data indicative of the date and time tracked by the mobile device 604. The clock 518 continues to update the current date and time thereafter as time passes. In an implementation, in response to the user 612 indicating to update the clock 518 of the diabetes management device 402 with the date and time tracked by the mobile device 604, the update may be performed once or each time that the diabetes management device 402 and the mobile device 604 establish a data connection.

At 732, the mobile device 604 determines whether a confirmation regarding the updating of the date and time of the diabetes management device 402 has been received from the diabetes management device 402. If 732 is false, control may remain at 732. If the confirmation is not received for a predetermined period, the mobile device 604 may timeout and end or take one or more other suitable actions. If 732 is true, the mobile device 604 may display an indication that the date and time of the diabetes management device 402 has been successfully updated on the touch display 608 at 736, and control may continue with 740.

The mobile device 604 displays a question on the touch display 608 at 740, the question being directed to whether to configure the diabetes management device 402 to automatically wirelessly transmit bG sample data to the mobile device 604 each time a bG measurement is obtained. The user 612 can select whether or not to configure the diabetes management device 402 to automatically wirelessly transmit (push) bG sample data to the mobile device 604 via predetermined areas on the touch display 608 or providing other suitable user inputs.

The diabetes management device 402 may also display the question to the user 612 on the display 408. The user 612 may select whether to configure the diabetes management device 402 to automatically wirelessly transmit bG sample data to the mobile device 604 via the diabetes management device 402. If the user 614 inputs his or her selection via the diabetes management device 402, the diabetes management device 402 wirelessly transmits an indicator of the selection to the mobile device 604.

At 744, the mobile device 604 determines whether the user 612 has input his or her selection as to whether to configure the diabetes management device 402 to automatically wirelessly transmit bG sample data to the mobile device 604. If not, control may return to 740 to keep displaying the question. If the user 612 has not input his or her selection for a predetermined period, the mobile device 604 may timeout and end or take one or more other suitable actions. If the user 612 has declined to configure the diabetes management device 402 to automatically wirelessly transmit bG sample data to the mobile device 604, control may transfer to 760 (FIG. 8B, discussed further below) or configuration of the diabetes management device 402 may end. If the user 612 has indicated to configure the diabetes management device 402 to automatically wirelessly transmit bG sample data to the mobile device 604, control continues with 748.

The mobile device 604 wirelessly transmits a request to the diabetes management device 402 at 748, the request being to configure the diabetes management device 402 to automatically transmit bG sample data to the mobile device 604. The diabetes management device 402 may, for example, alter a predetermined memory location in response to the request. Based on the request, when a bG measurement is later obtained, the diabetes management device 402 will automatically attempt to wirelessly transmit bG sample data indicative of the bG measurement to the mobile device 604.

At 752, the mobile device 604 determines whether a confirmation of the updating of the automatic transmission of bG sample data feature of the diabetes management device 402 has been received from the diabetes management device 402. If 752 is false, control may remain at 752. If the confirmation has not been received for a predetermined period, the mobile device 604 may timeout and end or take one or more other suitable actions. If 752 is true, the mobile device 604 may display, on the touch display 608, an indication that diabetes management device 402 has been successfully configured to automatically transfer bG sample data to the mobile device 604 at 756, and control may continue with 760.

At 760 (FIG. 8B), the mobile device 604 displays a question on the touch display 608, the question being directed to whether to register the diabetes management device 402 with the manufacturer of the diabetes management device 402. The user 612 can select whether or not to register the diabetes management device 402 via predetermined areas on the touch display 608 or providing other suitable user inputs.

The diabetes management device 402 may also display the question (whether to register the diabetes management device 402 with the manufacturer) to the user 612 on the display 408 of the diabetes management device 402. The user 612 may select whether to register the diabetes management device 402 via the diabetes management device 402. If the user 612 inputs his or her selection via the diabetes management device 402, the diabetes management device 402 wirelessly transmits an indicator of the selection to the mobile device 604.

At 764, the mobile device 604 determines whether the user 612 has input his or her selection as to whether to register the diabetes management device 402 with the manufacturer. If not, control may return to 760 to keep displaying the question. If the user 612 has not input his or her selection for a predetermined period, the mobile device 604 may timeout and end or take one or more other suitable actions. If the user 612 has declined to register the diabetes management device 402, configuration of the diabetes management device 402 may end. If the user 612 has indicated to register the diabetes management device 402 with the manufacturer, control continues with 768.

The mobile device 604 displays a registration user interface (UI) on the touch display 608 at 768. The registration UI may include a plurality of fields into which the user 612 can enter patient identifiable data of the user 612, such as first name, last name, middle initial or name, birth date, street address, city, state, zip code, contact telephone number, and/or other patient identifiable data of the user 612. The mobile device 604 receives the patient identifiable data input by the user 612 at 772. The mobile device 604 may also selectively display the physical character layout on the touch display 608 to facilitate entry of the patient identifiable data.

At 780, the mobile device 604 generates registration data based on the device data for the diabetes management device 402 and the patient identifiable data of the user 612. For example, the mobile device 604 associates the device data with the patient identifiable data. The mobile device 604 transmits the registration data (including the device data and the patient identifiable data) to a registration server 800 of the manufacturer at 784, for example, over the Internet. Control may then end.

The ability to enter the patient identifiable data using the mobile device 604 may ease entry of the patient identifiable data relative to using the diabetes management device 402 due to the limited UI and display of the diabetes management device 402. Registration of the diabetes management device 402 may therefore be made relatively easy using the mobile device 604. Even if the patient identifiable data was successfully entered into the diabetes management device 402, the diabetes management device 402 may still be unable to register the diabetes management device 402 with the manufacturer due to inability of the diabetes management device 402 to communicate with the registration server 800.

Once the diabetes management device 402 has been registered with the manufacturer, the manufacturer can contact the user 612, the diabetes management device 402 can be updated, etc. in compliance with requirements of one or more regulatory bodies, such as the U.S. Food and Drug Administration (FDA). For example, the device data that is transmitted during the registration can be used to identify a version of code executed by the diabetes management device 402. If an updated version of the code is released, the user 612 can be contacted. The user 612 could update the code executed by the diabetes management device 402, for example, by downloading the new code via the mobile device 604 and transferring the new code from the mobile device 604 to the diabetes management device 402. An example of such a system and method can be found in commonly assigned U.S. patent application Ser. No. 13/195,893, filed on Aug. 2, 2011, which is incorporated herein in its entirety.

Additionally, the ability to correctly update the date and time of the diabetes management device 402 and to configure the diabetes management device 402 to automatically transmit bG sample data may be made relatively easy using the mobile device 604. bG sample data received from the diabetes management device 402 by the mobile device 604 may also be more comprehensively analyzed by the user 612 via the mobile device 604 due to the more powerful processing capabilities of the mobile device 604, the more extensive UI of the mobile device 604, and the increased connectivity of the mobile device 604.

The above provides an easy way to setup operation of the diabetes management device 402 with the diabetes management application executed on the mobile device 604, accurately set the date and time of the diabetes management device 402, and register the diabetes management device 402 with the manufacturer. Once the setup is complete, bG measurements obtained by the diabetes management device 402 may be automatically transmitted to the mobile device 604. However, the diabetes management device 402 can still take bG measurements during the setup if a bG test strip is inserted into the bG test strip port 420. By way of the mobile device 604, the user 612 can more comprehensively analyze their bG data and use the bG data to make decisions regarding management of diabetes.

Additionally, once the diabetes management device 402 is registered, consumable products, can be sent to the user 612 when needed. For example, the manufacturer may selectively send or have delivered the user 612 replacement batteries for the diabetes management device 402 to the address provided by the user 612. Additionally or alternatively, the manufacturer may selectively send or have delivered the user 612 additional bG test strips for use with the diabetes management device 402.

In a first feature, an automated method for registering a medical device via an application residing on a mobile computing device is described. The method includes: confirming, by the mobile computing device, a wireless communication link between the medical device and the mobile computing device hosting the application; requesting, by the mobile computing device, identifying data for the medical device via the wireless communication link; and receiving, by the mobile computing device, identifying data for the medical device via the wireless communication link, the identifying data for the medical device received in response to the request for identifying data. The method further includes: presenting, by the mobile computing device, an option to register the medical device on a display of the mobile computing device; receiving, by the mobile computing device, an affirmative indication to register the medical device; and requesting, by the mobile computing device, input of patient identifiable data for a user of the medical device, the request for input being performed in response to receiving the affirmative indication to register. The method further includes: receiving, by the mobile computing device, patient identifiable data for the user of the medical device in response to the request for input; associating, by the mobile computing device, the patient identifiable data for the user with the identifying data for the medical device to form registration data for the medical device; and registering, by the mobile computing device, the medical device with a manufacturer of the medical device using the registration data.

In further features, the identifying data for the medical device includes at least a model identifier of the medical device and a serial number of the model identifier.

In still further features, the presenting the option to register the medical device includes presenting the option to register the medical device on a touchscreen display of the mobile computing device.

In yet further features, the method further includes presenting, by the mobile computing device, a second option on the display to configure the medical device to automatically transmit medical data to the mobile computing device in response to measurement of the medical data by the medical device.

In further features, the medical data includes measured blood glucose (bG).

In still further features the method further includes presenting, by the mobile computing device, at least a partial keyboard on the display, the presentation of the at least a partial keyboard being performed in response to receiving the affirmative indication to register.

In yet further features, the method further includes presenting, by the mobile computing device, a second option on the display to update a first date and time tracked by the medical device to a second date and time tracked by the mobile computing device.

In still further features, the method further includes transmitting to the medical device, using the mobile computing device, the second date and time and a request to update the first date and time to the second date and time, the transmission being performed in response to receiving an affirmative indication to update the first date and time.

In yet further features, the method further includes transmitting the registration data, using the mobile computing device, to a remote data server.

In still further features, the method further includes transmitting the registration data, using the mobile computing device, to the remote data server via the Internet.

In a second feature, a coordinated method to setup a medical device using an application residing on a mobile computing device is described. The method includes: establishing, by the mobile computing device, a wireless communication link between the medical device and the mobile computing device hosting the application; requesting, by the mobile computing device, identifying data for the medical device via the wireless communication link; receiving, by the mobile computing device, identifying data for the medical device via the wireless communication link, the identifying data for the medical device received in response to the request for identifying data; and presenting, by the mobile computing device on a display of the mobile computing device, a first option to synchronize a first date and time tracked by the medical device with a second date and time tracked by the mobile computing device. The method further includes: receiving, by the mobile computing device, a first indication to synchronize the first date and time with the second date and time; transmitting, by the mobile computing device, the second date and time tracked the mobile computing device via the wireless communication link to the medical device, the sending being performed in response to the first indication to synchronize the first date and time with the second date and time; presenting, by the mobile computing device, a second option to configure the medical device to automatically wirelessly transmit medical data on the display of the mobile computing device; receiving, by the mobile computing device, a second indication to configure the medical device to automatically wirelessly transmit medical data; and transmitting to the medical device, by the mobile computing device, a request to configure the medical device to automatically wirelessly transmit medical data, the transmission being performed in response to receiving the second indication. The method further includes: presenting on the display, by the mobile computing device, a third option to register the medical device with a manufacturer of the medical device; receiving, by the mobile computing device, a third indication to register the medical device; requesting, by the mobile computing device, input of patient identifiable data for a user of the medical device, the request for input being performed in response to receiving the third indication; receiving, by the mobile computing device, the patient identifiable data for the user of the medical device in response to the request for input; associating, by the mobile computing device, the patient identifiable data for the user with the identifying data for the medical device to form registration data for the medical device; and registering, by the mobile computing device, the medical device with the manufacturer of the medical device using the registration data.

In further features, the method further includes transmitting the registration data, using the mobile computing device, to a remote data server.

In still further features, the identifying data for the medical device includes at least a model identifier of the medical device and a serial number of the model identifier.

In yet further features, the presenting the third option to register the medical device includes presenting the option to register the medical device on a touchscreen display of the mobile computing device.

In further features, the medical data includes measured blood glucose (bG).

In still further features, the method further includes presenting, by the mobile computing device, at least a partial keyboard on the display, the presentation of the at least a partial keyboard being performed in response to receiving the third indication.

In yet further features, the method further includes: receiving, by the mobile computing device, an indication from the medical device that the medical device set the first date and time to the second date and time; and presenting on the display, by the mobile computing device, a confirmation of the synchronization of the first date and time with the second date and time.

In further features, the method further includes wirelessly receiving, by the mobile computing device, the medical data wirelessly transmitted by the medical device.

In still further features, the patient identifiable data includes at least a name of the user and contact information for the user.

In a third feature, a mobile computing device executing an application for coordinating operation of the mobile computing device with a handheld diabetes management device is described. The mobile computing device includes: a touchscreen display; a processor; and memory. The memory includes instructions that, when executed, cause the mobile computing device to: establish a wireless communication link between the handheld diabetes management device and the mobile computing device; receive identifying data for the handheld diabetes management device via the wireless communication link; request identifying data for the handheld diabetes management device via the wireless communication link; present a first option on the touchscreen display to synchronize a first date and time tracked by the handheld diabetes management device with a second date and time tracked by the mobile computing device; and transmit the second data and time via the wireless communication link to the handheld diabetes management device in response to a first indication to synchronize the first date and time with the second date and time. When executed, the instructions further cause the mobile computing device to: present a second option on the touchscreen display to configure the handheld diabetes management device to automatically wirelessly transmit medical data; transmit, to the handheld diabetes management device, a request to configure the handheld diabetes management device to automatically wirelessly transmit medical data in response to a second indication to configure the handheld diabetes management device to automatically wirelessly transmit medical data; present a third option on the touchscreen display to register the handheld diabetes management device with a manufacturer of the handheld diabetes management device; present a request on the touchscreen display to input of patient identifiable data for a user of the handheld diabetes management device in response to a third indication to register the handheld diabetes management device; and transmit the identifying data and the patient identifiable data to a registration server.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

In this application, including the definitions below, the term module may be replaced with the term circuit. The term module may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this application may be partially or fully implemented by one or more computer programs executed by one or more processors. The computer programs include processor-executable instructions that are stored on at least one non-transitory tangible computer readable medium. The computer programs may also include and/or rely on stored data.

What is claimed is:

1. An automated method for registering a medical device via an application residing on a mobile computing device, comprising:
    confirming, by the mobile computing device, a wireless communication link between the medical device and the mobile computing device hosting the application;
    requesting, by the mobile computing device, identifying data for the medical device via the wireless communication link;
    receiving, by the mobile computing device, identifying data for the medical device via the wireless communication link, the identifying data for the medical device received in response to the request for identifying data;
    presenting, by the mobile computing device, an option to register the medical device on a display of the mobile computing device;
    receiving, by the mobile computing device, an affirmative indication to register the medical device;
    requesting, by the mobile computing device, input of patient identifiable data for a user of the medical device, the request for input being performed in response to receiving the affirmative indication to register;
    receiving, by the mobile computing device, patient identifiable data for the user of the medical device in response to the request for input;
    associating, by the mobile computing device, the patient identifiable data for the user with the identifying data for the medical device to form registration data for the medical device;
    registering, by the mobile computing device, the medical device with a manufacturer of the medical device using the registration data;
    presenting, by the mobile computing device, a second option on the display to update a first date and time tracked by the medical device to a second date and time tracked by the mobile computing device; and
    transmitting to the medical device, using the mobile computing device, the second date and time and a request to update the first date and time to the second date and time, the transmission being performed in response to receiving an affirmative indication to update the first date and time.

2. The method of claim 1 wherein the identifying data for the medical device includes at least a model identifier of the medical device and a serial number of the model identifier.

3. The method of claim 1 wherein the presenting the option to register the medical device includes presenting the option to register the medical device on a touchscreen display of the mobile computing device.

4. The method of claim 1 further comprising presenting, by the mobile computing device, a second option on the display to configure the medical device to automatically transmit medical data to the mobile computing device in response to measurement of the medical data by the medical device.

5. The method of claim 4 wherein the medical data includes measured blood glucose (bG).

6. The method of claim 1 further comprising presenting, by the mobile computing device, at least a partial keyboard on the display, the presentation of the at least a partial keyboard being performed in response to receiving the affirmative indication to register.

7. The method of claim 1 further comprising transmitting the registration data, using the mobile computing device, to a remote data server.

8. The method of claim 7 further comprising transmitting the registration data, using the mobile computing device, to the remote data server via the Internet.

9. A mobile computing device executing an application for coordinating operation of the mobile computing device with a handheld diabetes management device, the mobile computing device comprising:
    a touchscreen display;
    a processor; and
    memory including instructions that, when executed, cause the mobile computing device to:

establish a wireless communication link between the handheld diabetes management device and the mobile computing device;

receive identifying data for the handheld diabetes management device via the wireless communication link;

request identifying data for the handheld diabetes management device via the wireless communication link;

present a first option on the touchscreen display to synchronize a first date and time tracked by the handheld diabetes management device with a second date and time tracked by the mobile computing device;

transmit the second data and time via the wireless communication link to the handheld diabetes management device in response to a first indication to synchronize the first date and time with the second date and time;

present a second option on the touchscreen display to configure the handheld diabetes management device to automatically wirelessly transmit medical data;

transmit, to the handheld diabetes management device, a request to configure the handheld diabetes management device to automatically wirelessly transmit medical data in response to a second indication to configure the handheld diabetes management device to automatically wirelessly transmit medical data;

present a third option on the touchscreen display to register the handheld diabetes management device with a manufacturer of the handheld diabetes management device;

present a request on the touchscreen display to input of patient identifiable data for a user of the handheld diabetes management device in response to a third indication to register the handheld diabetes management device; and transmit the identifying data and the patient identifiable data to a registration server.

10. A coordinated method to setup a medical device using an application residing on a mobile computing device, comprising:

establishing, by the mobile computing device, a wireless communication link between the medical device and the mobile computing device hosting the application;

requesting, by the mobile computing device, identifying data for the medical device via the wireless communication link;

receiving, by the mobile computing device, identifying data for the medical device via the wireless communication link, the identifying data for the medical device received in response to the request for identifying data;

presenting, by the mobile computing device on a display of the mobile computing device, a first option to synchronize a first date and time tracked by the medical device with a second date and time tracked by the mobile computing device;

receiving, by the mobile computing device, a first indication to synchronize the first date and time with the second date and time;

transmitting, by the mobile computing device, the second date and time tracked the mobile computing device via the wireless communication link to the medical device, the sending being performed in response to the first indication to synchronize the first date and time with the second date and time;

presenting, by the mobile computing device, a second option to configure the medical device to automatically wirelessly transmit medical data on the display of the mobile computing device;

receiving, by the mobile computing device, a second indication to configure the medical device to automatically wirelessly transmit medical data;

transmitting to the medical device, by the mobile computing device, a request to configure the medical device to automatically wirelessly transmit medical data, the transmission being performed in response to receiving the second indication;

presenting on the display, by the mobile computing device, a third option to register the medical device with a manufacturer of the medical device;

receiving, by the mobile computing device, a third indication to register the medical device;

requesting, by the mobile computing device, input of patient identifiable data for a user of the medical device, the request for input being performed in response to receiving the third indication;

receiving, by the mobile computing device, the patient identifiable data for the user of the medical device in response to the request for input;

associating, by the mobile computing device, the patient identifiable data for the user with the identifying data for the medical device to form registration data for the medical device; and registering, by the mobile computing device, the medical device with the manufacturer of the medical device using the registration data.

11. The method of claim 10 wherein the patient identifiable data includes at least a name of the user and contact information for the user.

12. The method of claim 10 further comprising transmitting the registration data, using the mobile computing device, to a remote data server.

13. The method of claim 10 wherein the identifying data for the medical device includes at least a model identifier of the medical device and a serial number of the model identifier.

14. The method of claim 10 wherein the presenting the third option to register the medical device includes presenting the option to register the medical device on a touchscreen display of the mobile computing device.

15. The method of claim 10 wherein the medical data includes measured blood glucose (bG).

16. The method of claim 10 further comprising presenting, by the mobile computing device, at least a partial keyboard on the display, the presentation of the at least a partial keyboard being performed in response to receiving the third indication.

17. The method of claim 10 further comprising:
receiving, by the mobile computing device, an indication from the medical device that the medical device set the first date and time to the second date and time; and
presenting on the display, by the mobile computing device, a confirmation of the synchronization of the first date and time with the second date and time.

18. The method of claim 10 further comprising wirelessly receiving, by the mobile computing device, the medical data wirelessly transmitted by the medical device.

* * * * *